(12) United States Patent
Macciocchi

(10) Patent No.: US 6,858,847 B1
(45) Date of Patent: Feb. 22, 2005

(54) CIRCUIT AND METHOD FOR ENERGY DISCRIMINATION OF COINCIDENT EVENTS IN COINCIDENCE DETECTING GAMMA CAMERA SYSTEM

(75) Inventor: Fred Macciocchi, Des Plaines, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 820 days.

(21) Appl. No.: 09/168,153

(22) Filed: Oct. 8, 1998

(51) Int. Cl.⁷ .............................................. G01T 1/164

(52) U.S. Cl. .............................................. 250/363.03

(58) Field of Search .................................. 250/363.03

(56) References Cited

U.S. PATENT DOCUMENTS 3,955,088 A 5/1976 Muehllehner et al.
5,866,907 A * 2/1999 Drukier et al. ............. 250/366
6,057,551 A * 5/2000 Tararine ................ 250/363.03

FOREIGN PATENT DOCUMENTS

CA 1149972 A * 7/1983 ............ 250/363.03

* cited by examiner

Primary Examiner—Constantine Hannaher

(57) ABSTRACT

A positron imaging system includes a pair of scintillation detectors for detecting a pair of gamma rays produced by annihilation of a positron within a distribution field, such as within a patient. An energy level determination circuit determines the energy levels of the detected gamma rays, and timing circuits determine whether the gamma rays have been detected by the scintillation detectors within a predetermined time interval. Only if the determined energy levels of each of the pair of gamma rays meet predetermined magnitude requirements and detection of the pair of gamma rays has occurred within the predetermined time interval, are signals corresponding to said gamma rays inputted to processing circuitry for calculating the spatial location of the positron. According to a further aspect of the invention, a circuit for separating piled-up gamma ray events includes a delay and a controllable attenuator for delaying and simultaneously attenuating a signal outputted by the detector, and a comparator for comparing the delayed signal with the attenuated signal, to thereby output separate electrical pulses representing the separate events.

14 Claims, 8 Drawing Sheets

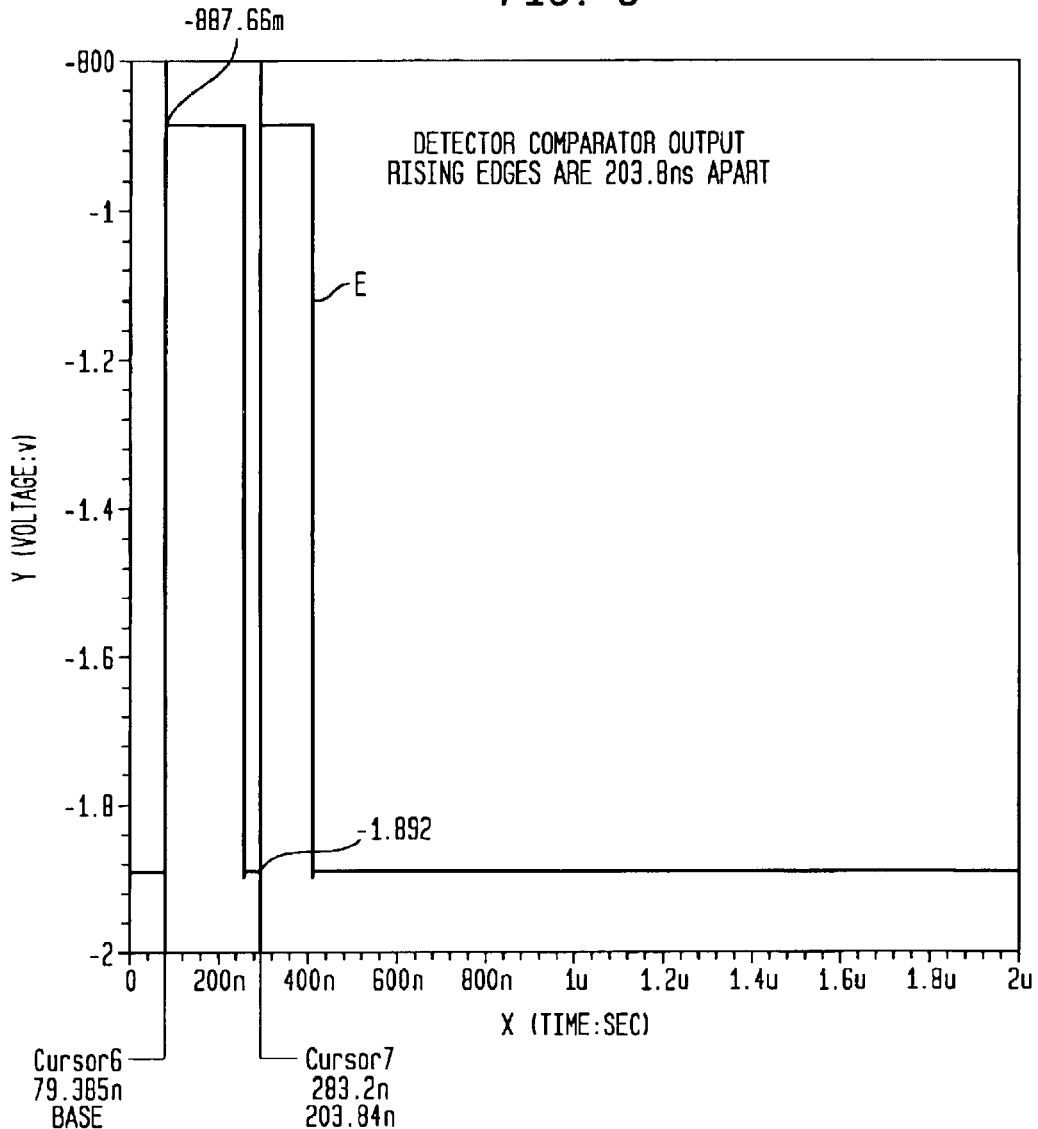

CIRCUIT AND METHOD FOR ENERGY DISCRIMINATION OF COINCIDENT EVENTS IN COINCIDENCE DETECTING GAMMA CAMERA SYSTEM

BACKGROUND OF THE INVENTION

1. Field of the Invention

The present invention generally relates to nuclear medicine, and systems for obtaining nuclear medicine images of a patient's body organs of interest. In particular, the present invention relates to systems and methods for obtaining nuclear medicine images by detecting coincident events resulting from positron annihilation.

2. Description of the Background Art

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce a three-dimensional image for diagnosing the biochemistry or physiology in a specific organ, tumor or other metabolically active site.

In PET, events are detected from the decay or annihilation of a positron. As shown in FIG. 1, when a positron 100 is annihilated within a subject 10, two 511 KeV gamma rays 101a and 101b are simultaneously produced which travel in approximately opposite directions. Two scintillation detectors 12a and 12b are positioned on opposite sides of the patient 10 such that each detector will produce an electrical pulse in response to the interaction of the gamma rays 101a and 101b with a scintillation crystal 14. In order to distinguish the detected positron annihilation events from background radiation or random events, the events must be coincident in each detector in order to be counted as "true" events.

True events result when the two 511 KeV photons from a single positron annihilation travel directly to opposite detectors and are absorbed by the respective scintillation crystals. A second type of event occurs when one or both of the 511 KeV photons is deflected from its original trajectory, either in the patient or in the crystal. This is known as Compton interaction or scatter. Because of their high energy, the percentage of 511 KeV photons which interact with the scintillation crystal without scatter is relatively small. Most of the 511 KeV photons pass through the crystal without interaction, while over half of the 511 KeV photons that do interact with the crystal undergo Compton scatter. Consequently, simply increasing the sensitivity of the crystal will result in the detection of an increased number of invalid events. As such, it is desirable in coincidence detection imaging to improve the accuracy of acquired images, by increasing the number of true events detected.

It is known in the prior art to use Compton events in positron imaging, see U.S. Pat. No. 3,955,088 to Muehllehner et al. Compton events may be usefully added to the stored distribution because the location of the origin of the event in the object under study can be calculated from the point of interaction of the Compton event in the crystal.

However, in the prior art as exemplified by the '088 patent, a pair of events is passed on for processing by position computing circuitry if they occur within a specific time interval or timing window. This procedure results in non-productive use of the processing circuitry in computing the position of events later determined to be invalid.

Additionally, the prior art rejects a significant number of valid events because of the phenomenon known as "pile-up." Pile-up occurs when two events occur so close together in time that their amplitudes are erroneously combined in the detector. Such "piled-up" events typically are rejected by prior art detectors because they are detected as a single event with an energy level that exceeds the predetermined maximum energy threshold. Thus, there remains a need in the art to improve upon the throughput speed and accuracy of acquired images in a positron coincidence imaging system.

SUMMARY OF THE INVENTION

The present invention solves the existing need by providing a circuit and method for detecting coincidence events in a nuclear imaging system by incorporating energy discrimination into the coincidence detector. By discriminating detected events on the basis of their energy levels in addition to timing requirements, only those events meeting both the timing and energy requirements are allowed to be passed to position processing electronics for further processing. In this way, time-consuming processing of events ultimately determined to be invalid or unusable is either eliminated or substantially reduced, resulting in increased throughput and accuracy of acquired images. Accuracy is further increased through the use of a modified constant fraction discriminator circuit to separate events which are piled up, such that each event may be detected and counted in the acquisition of an image.

BRIEF DESCRIPTION OF THE DRAWINGS

The invention will become more clearly understood from the following detailed description in connection with the accompanying drawings, in which:

FIGS. 5–8 are graphs of output signals at various locations in the circuit of FIG. 4.

DETAILED DESCRIPTION OF THE PREFERRED EMBODIMENTS

Figure 1:
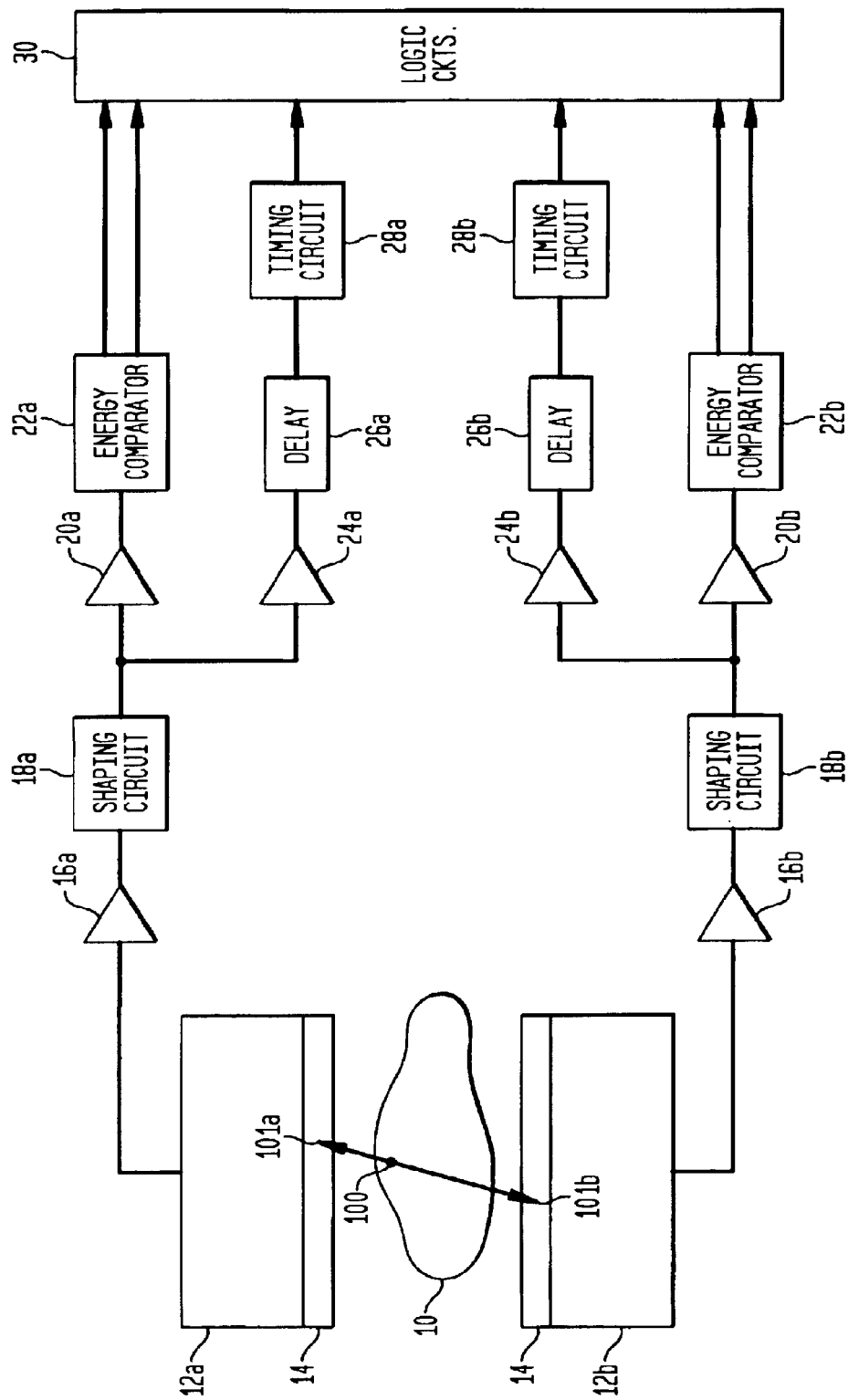
FIG. 1 is a block diagram of a circuit for determining coincidence and energy level requirements of detected events according to one preferred embodiment of the invention.

FIG. 1 illustrates a block diagram according to one preferred embodiment of the invention, wherein an object under study 10 (such as a patient given a dose of a radiopharmaceutical) is placed between two detectors 12a and 12b. Each detector includes a scintillation crystal 14 (typically made of thallium activated sodium iodide (NaI), a plurality of photodetector devices (typically an array of photomultiplier tubes) and associated signal processing circuitry.

A positron decay 100 occurring in a region of interest in the object 10 results in the emission of two 511 KeV gamma rays 101a and 101b, which travel in opposite directions and are respectively absorbed in scintillation crystals 14 of detectors 12a and 12b. The interaction of the gamma rays with the crystal produces a flash of light which is detected by the photodetector array (not shown) and converted into an electrical pulse which is output from the detectors as a voltage signal. The output signals are respectively inputted to differential gain amplifier stages 16a, 16b. The output signal is amplified and inverted in the gain stage to provide proper signal levels for the shaping circuit 18a, 18b. The gain stages 16a, 16b typically provide a gain of +2. The shaping circuits 18a, 18b are used to shorten or "clip" the signals so that they are of proper length for further processing.

After shaping, the output signals are applied to gain stages 20a, 20b and 24a, 24b. Gain stages 20a, 20b provide a gain of +5, after which the signal is inputted to energy comparator circuit 22a, 22b. Gain stages 24a, 24b provide a gain of +10 for application of the signals to timing circuits 28a, 28b. Delay lines 26a and 26b are provided between gain stages 24 and timing circuits 28 to delay the output signals from entering the timing circuits until sufficient time has elapsed for the output signals to reach a predetermined percentage of their total energy level to be measured in the energy comparator circuits.

Figure 3:
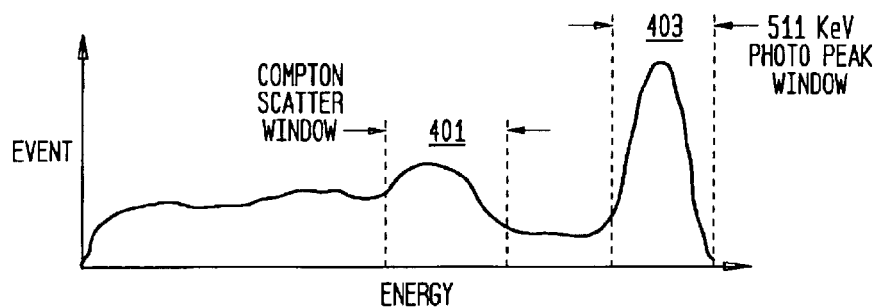
FIG. 3 is a graph of the energy distribution of a scintillation event from positron annihilation.

As shown in FIG. 3, if the energy of the output signal falls in either the Compton window 401 or the photopeak window 403, the energy comparator will output an appropriate signal to the logic circuits 30. If both signals occur within a predetermined time interval (on the order of 10–15 nanoseconds) an appropriate timing signal will be applied to the logic circuits 30. If the timing signal and the energy signal are both present, the logic circuits transmit a signal back to the detector which causes the event signal to be passed on to the processing electronics for further processing to be included in the image. If either of the timing or energy signals is not present, the event is not processed by the processing circuitry, but is discarded, thereby saving valuable computing time.

Figure 2A:
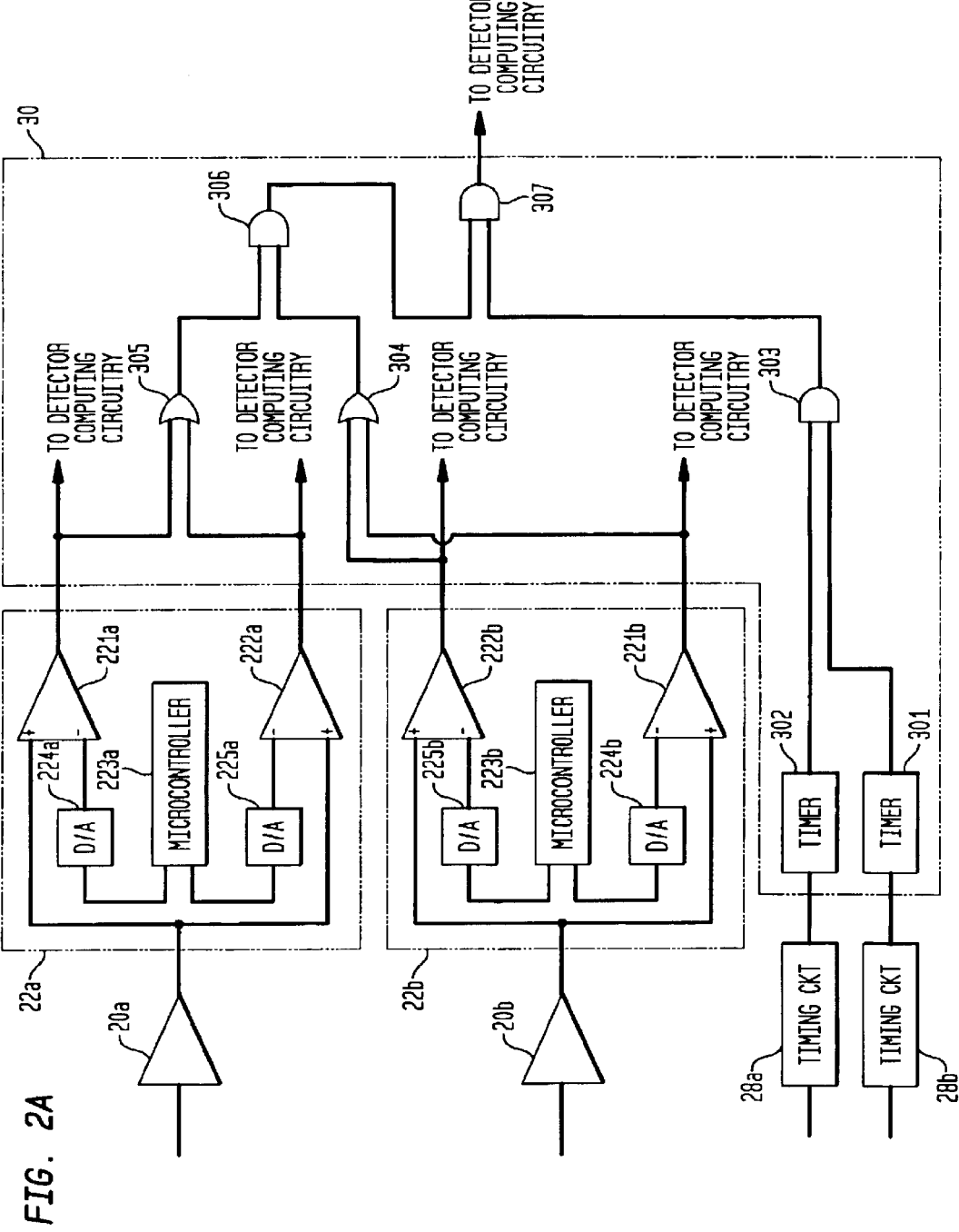
FIG. 2A is a schematic diagram of the energy comparator and logic circuits of FIG. 1 according to one embodiment of the invention.

FIG. 2A is a schematic diagram showing details of the energy comparator circuits 22a, 22b and logic circuits 30 according to a first embodiment of the invention. Each energy comparator includes a dual comparator 221, 222. The inverting input of comparator 221 is provided with the photopeak energy level outputted by microcontroller 223 through a digital-to-analog (D/a) converter 224. The inverting input of comparator 222 is provided with the Compton scatter energy level produced by the microcontroller and applied to D/a converter 225. The output event signal is applied to the noninverting inputs of each comparator 221, 222. The outputs of comparators 221a and 222a are inputted to OR gate 305, and the outputs of comparators 221b and 222b are inputted to OR gate 304. The outputs of OR gates 304 and 305 are inputted to AND gate 306. The outputs of the comparators may be also sent to the detector computing circuitry for use in position calculation. As such, a signal will be outputted by AND gate 306 if the energy levels of the event signals from each detector are in either the Compton scatter window or the photopeak window.

As shown, the comparators 221 and 222 actually compare the energy level of the signal with the lower threshold value of the respective Compton and photopeak energy windows as shown in FIG. 3. In practice, the probability that an event rising above the Compton window lower threshold level but not above the lower photopeak window threshold level will fall within the Compton window is such that the upper Compton window threshold need not be tested for the purpose served by the invention. Similarly, the probability that an event which crosses the lower photopeak window threshold level will fall within the photopeak window is such that the upper photopeak window threshold need not be tested. However, it is possible to substitute single channel analyzers for each of the dual comparators to thereby determine whether energy levels fall precisely within each defined window. Because such single channel analyzers are well known in the art, their operation will not be further described.

Figure 2B:
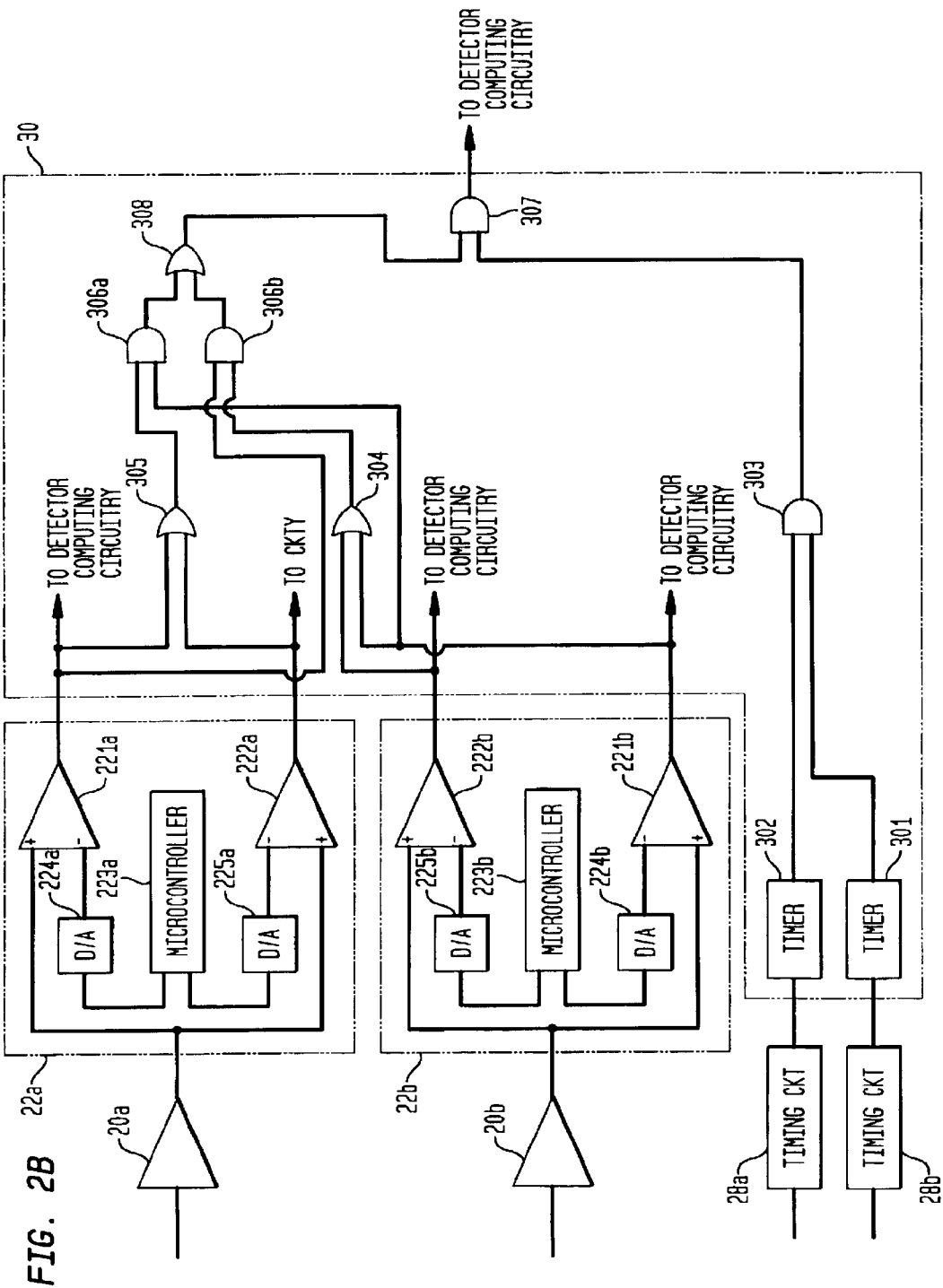
FIG. 2B is a schematic diagram of the energy comparator and logic circuits of FIG. 1 according to a second embodiment of the invention.

A second embodiment of the energy comparator circuits and logic circuits is shown in FIG. 2B. In this embodiment, a third OR gate 308 is supplied with the outputs from the photopeak level comparators 221a, 221b of each detector. The output of OR gate 308 is inputted to a three-input AND gate 306a, along with the outputs from OR gates 304 and 305. Thus, an output signal from AND gate 306a will be produced only if at least one of the events in each detector is a photopeak event. This embodiment prevents a positron event from being counted in the acquired image if both photons are Compton scatter photons. In such case, there exists a significant probability that the photons were scattered within the patient's body, and thus the computation of the point of origin of the positron event would be less reliable than desired.

Timing circuits 28a and 28b provide start signals to timers 301, 302 in response to receipt of event signals. In response to the start signals, each timer produces an output signal for a predetermined period time (such as 10–15 nanoseconds). The output signals from the timers are inputted to AND gate 303. Thus, AND gate 303 will produce an output signal only if both events trigger their respective timers within the predetermined interval.

The outputs of AND gates 303 and 304 are provided to AND gate 307. If signals from AND gate 303 and AND gate 306 are present at the same time, AND gate 307 will output a signal which will be applied to the detector computing circuitry to allow the event signal to be passed into the computing circuitry for further processing.

Figure 4:
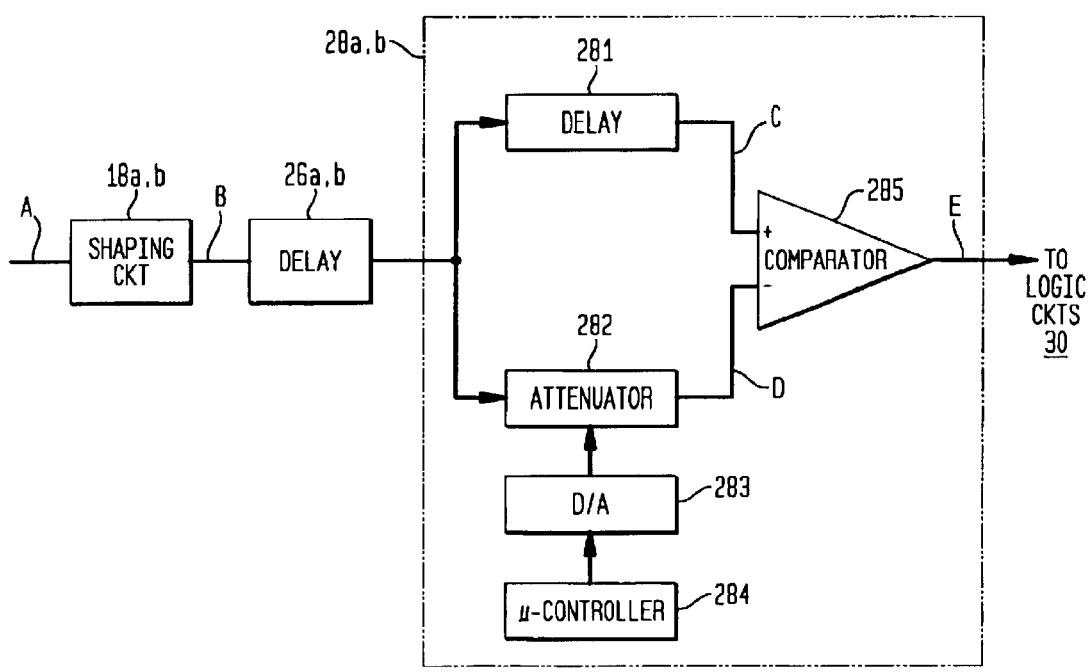
FIG. 4 is a schematic diagram of a timing circuit according to one embodiment of the present invention.
Figure 5:
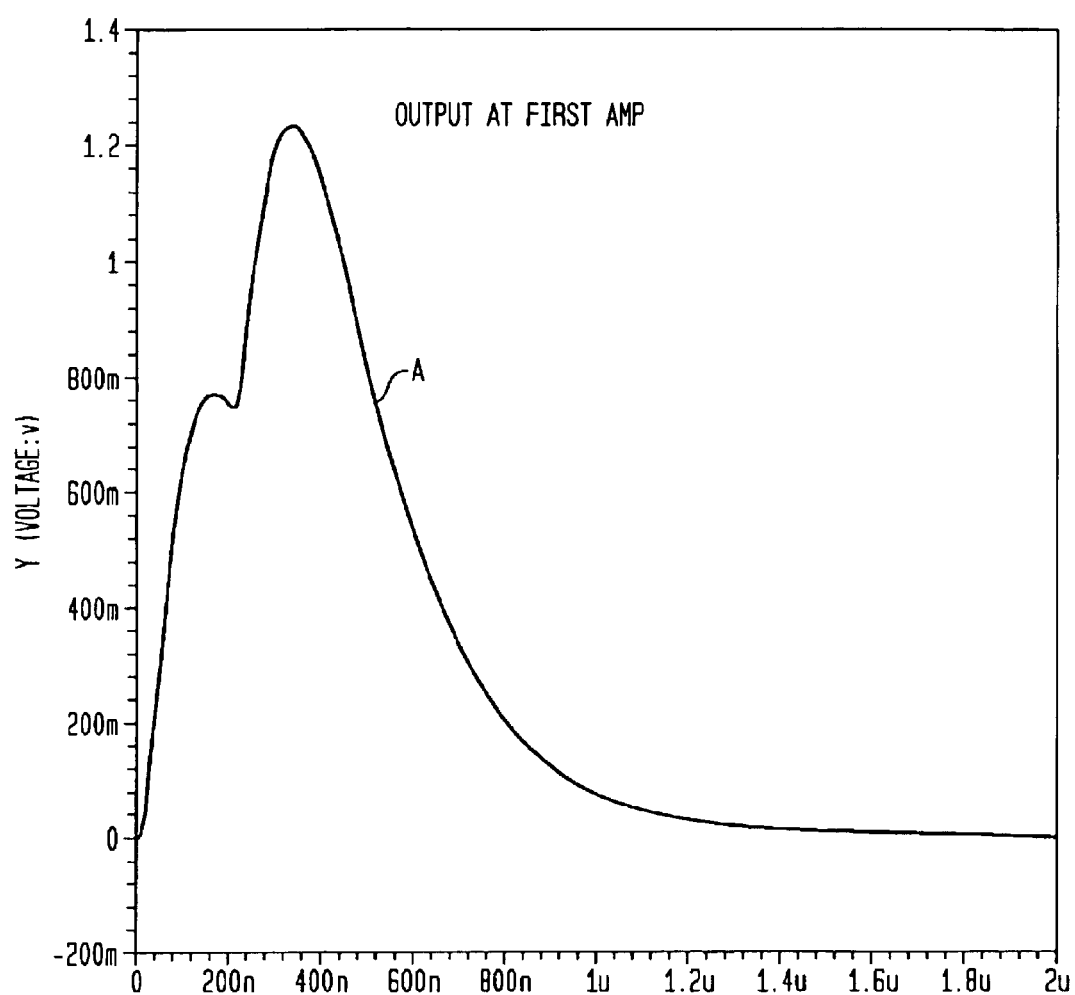
Figure 6:
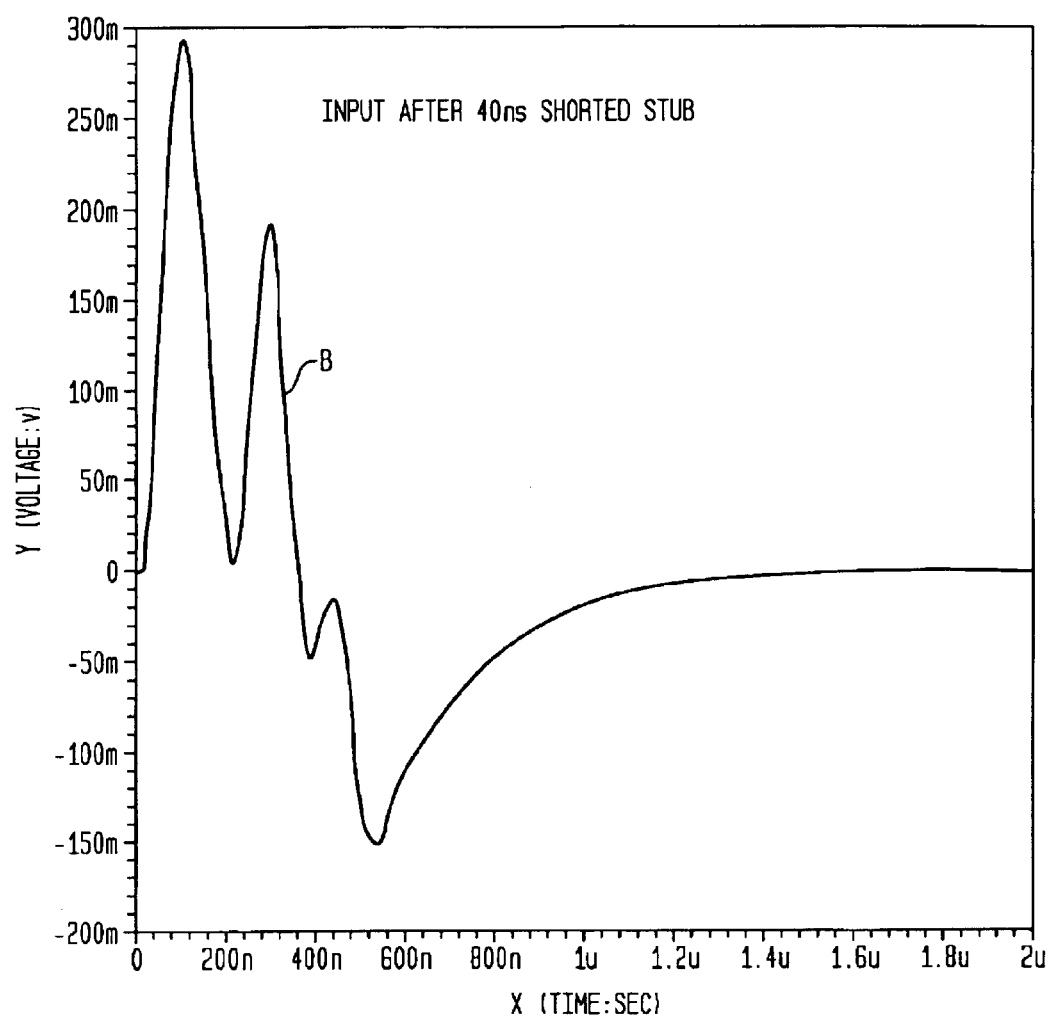
Figure 7:
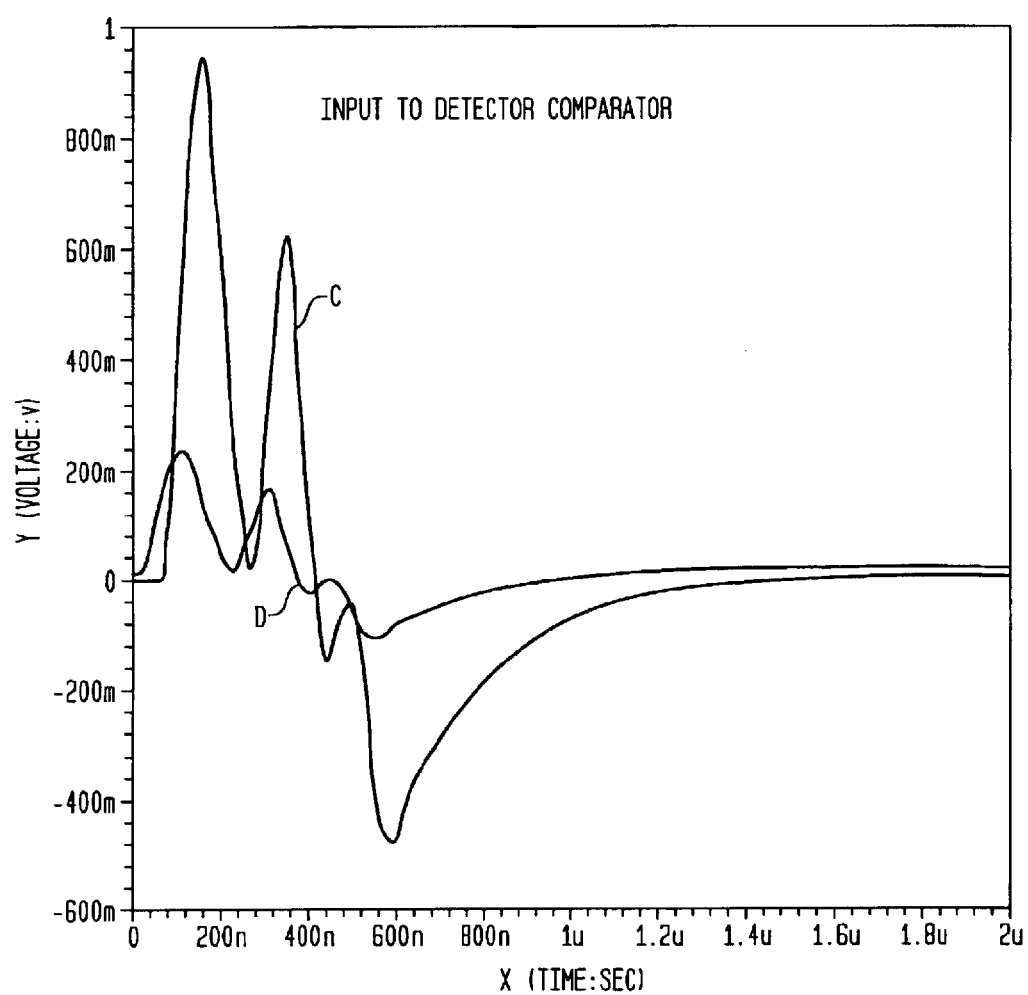

FIG. 4 shows the details of timing circuits 28a, 28b which enable the circuit to discriminate between events that are piled up. Two piled-up events entering shaping circuit 18a, b at a are shown in FIG. 5. The shaped events outputted by the shaping circuit at point B are shown in FIG. 6. The output of the shaping circuit is delayed in delay line 26a, b and the output is sent to a further delay line 281, the output of which at point C is shown in FIG. 7.

The delayed output of the shaping circuit from delay line 26a, b is also inputted to an attenuator 282. The attenuator also receives an input from a microcontroller 284 via D/a converter 283 which controls the amount of attenuation of the signal by a predetermined factor. The output of the attenuator at point D is also shown in FIG. 7. As shown, two distinct events are present, with the signal C crossing above the signal D twice. The output of the delay line 281 is applied to the non-inverting input of a comparator 285, and the output of the attenuator is applied to the inverting input of the comparator 285 such that the comparator will output two separate pulses at point E as shown in FIG. 8. The output pulses at E are independent of amplitude over a range similar to the output of a constant fraction discriminator. The attenuated signal is shifted by the signal from the microcontroller so as to allow multiple pulses to be generated by the comparator from piled up event pulses. The separation of the piled up events allows these events to be used in the acquisition of the image instead of being discarded as in the prior art. This allows a greater number of otherwise valid events to be used in the acquisition of the image, which improves the contrast quality of the resulting image.

The invention having been described, it will be apparent to those skilled in the art that the same may be varied in many ways without departing from the spirit and scope of the invention. Any and all such modifications are intended to be included within the scope of the following claims.

What is claimed is:

1. A method for acquiring images from a radiation field, comprising the steps of:

detecting a pair of gamma rays produced by annihilation of a positron within said field;

determining energy levels of each of said pair of gamma rays;

determining whether detection of said pair of gamma rays occurs within a predetermined time interval;

calculating the spatial location of said positron by calculating the spatial location of each of said pair of gamma rays only if the determined energy levels of each of said pair of gamma rays meet predetermined magnitude requirements, and detection of said pair of gamma rays has occurred within said predetermined time interval; and adding the calculated positron spatial location to a stored distribution of calculated positron spatial locations representing said image.

2. A method for acquiring images as set forth in claim 1, wherein the step of determining energy levels comprises the step of determining, for each of said pair of gamma rays, whether its energy is greater than a lower threshold value of a predefined photopeak energy window.

3. A method for acquiring images as set forth in claim 1, wherein the step of determining energy levels comprises the step of determining, for each of said pair of gamma rays, whether its energy is greater than a lower threshold value of a predefined Compton scatter energy window.

4. A method for acquiring images as set forth in claim 3, wherein the step of determining energy levels further comprises the step of determining, for each of said pair of gamma rays, whether its energy is greater than a lower threshold value of a predefined photopeak energy window.

5. A method for acquiring images as set forth in claim 4, wherein said predetermined magnitude requirements are met when the energy level of one of said pair of gamma rays is greater than said lower threshold value of said predefined photopeak energy window and the energy level of the other of said pair of gamma rays is greater than said lower threshold value of said predefined Compton scatter energy window.

6. A method for acquiring images as set forth in claim 4, wherein said predetermined magnitude requirements are met when the energy level of each of said pair of gamma rays is greater than said lower threshold value of said predefined Compton scatter energy window.

7. A method for acquiring images as set forth in claim 1, wherein the step of detecting a pair of gamma rays comprises the steps of converting light emitted from interaction of each of said gamma rays with a detector into an electrical signal, simultaneously delaying said electrical signal by a predetermined delay and attenuating said electrical signal by a preselected factor, comparing the delayed electrical signal with the attenuated electrical signal in a comparator and outputting the result of said comparison as one or more electrical pulses.

8. A system for acquiring images from a radiation field, comprising:

a pair of scintillation detectors for detecting a pair of gamma rays produced by annihilation of a positron within said field;

an energy level determination circuit coupled to each scintillation detector for determining energy levels of a respective one of said pair gamma rays;

a pair of timing circuits, each coupled to a respective scintillation detector, for determining whether said pair of gamma rays have been detected by said scintillation detectors within a predetermined time interval; and processing circuitry for calculating the spatial location of said positron by calculating the spatial location of each of said pair of gamma rays only if the determined energy levels of each of said pair of gamma rays meet predetermined magnitude requirements, and detection of said pair of gamma rays has occurred within said predetermined time interval.

9. A system for acquiring images as set forth in claim 8, wherein said energy level determination circuit determines, for each of said pair of gamma rays, whether its energy is greater than a lower threshold value of a predefined photopeak energy window.

10. A system for acquiring images as set forth in claim 8, wherein said energy level determination circuit determines, for each of said pair of gamma rays, whether its energy is greater than a lower threshold value of a predefined Compton scatter energy window.

11. A system for acquiring images as set forth in claim 10, wherein said energy level determination circuit determines, for each of said pair of gamma rays, whether its energy is greater than a lower threshold value of a predefined photopeak energy window.

12. A system for acquiring images as set forth in claim 11, wherein said predetermined magnitude requirements are met when the energy level of one of said pair of gamma rays is greater than said lower threshold value of said predefined photopeak energy window and the energy level of the other of said pair of gamma rays is greater than said lower threshold value of said predefined Compton scatter energy window.

13. A system for acquiring images as set forth in claim 11, wherein said predetermined magnitude requirements are met when the energy level of each of said pair of gamma rays is greater than said lower threshold value of said predefined Compton scatter energy window.

14. A system for acquiring images as set forth in claim 8, wherein each of said pair of scintillation detectors includes means for converting light emitted from interaction of each of said gamma rays with a scintillation crystal into an electrical signal, means for delaying said electrical signal by a predetermined delay and means for simultaneously attenuating said electrical signal by a preselected factor, and means for comparing the delayed electrical signal with the attenuated electrical signal and outputting the result of said comparison as one or more electrical pulses.

* * * * *